(12) United States Patent
Shah et al.

(10) Patent No.: US 11,433,115 B2
(45) Date of Patent: *Sep. 6, 2022

(54) GLYCOPEPTIDE ANTIBIOTICS LIQUID FORMULATIONS AND METHODS AND USES THEREOF

(71) Applicant: SOMERSET THERAPEUTICS, LLC, Hollywood, FL (US)

(72) Inventors: Mandar V. Shah, Somerset, NJ (US); Ilango Subramanian, Somerset, NJ (US); Veerappan Subramanian, Somerset, NJ (US)

(73) Assignee: SOMERSET THERAPEUTICS, LLC, Hollywood, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/512,321

(22) Filed: Oct. 27, 2021

(65) Prior Publication Data

US 2022/0133845 A1 May 5, 2022

Related U.S. Application Data

(60) Provisional application No. 63/107,919, filed on Oct. 30, 2020.

(51) Int. Cl.
| | | |
|---|---|---|
| *A61K 38/14* | (2006.01) | |
| *A61K 9/08* | (2006.01) | |
| *A61P 31/04* | (2006.01) | |
| *A61K 47/18* | (2017.01) | |

(52) U.S. Cl.
CPC ............... *A61K 38/14* (2013.01); *A61K 9/08* (2013.01); *A61K 47/183* (2013.01); *A61P 31/04* (2018.01)

(58) Field of Classification Search
None
See application file for complete search history.

(56) References Cited

U.S. PATENT DOCUMENTS

| | | | |
|---|---|---|---|
| 4,670,258 A | 6/1987 | Harris et al. | |
| 4,885,275 A | 12/1989 | Robison | |
| 8,778,873 B2 | 7/2014 | Chaudhary | |
| 10,039,804 B2 * | 8/2018 | Jasprica | A61K 47/183 |
| 10,188,697 B2 * | 1/2019 | Jasprica | A61K 9/08 |
| 2014/0260098 A1 | 9/2014 | Teo et al. | |

FOREIGN PATENT DOCUMENTS

| | | | |
|---|---|---|---|
| JP | 2008/201778 A | 9/2008 | |
| WO | WO 1997/19690 | 6/1997 | |
| WO | WO-0059528 A1 * | 10/2000 | ............ C07K 9/008 |
| WO | WO 2001/82971 A2 | 11/2001 | |
| WO | WO 2014/085526 A1 | 6/2014 | |

OTHER PUBLICATIONS

"Opinion of the Scientific Panel on Food Additives, Flavourings, Processing Aids and Materials in Contact with Food (AFC) on a request from the Commission related to N-Acetyl-L-Methionine for use in foods for special medical purposes." The EFSA Journal (2003), 22:1-10.
"Estimating the Maximum Safe Starting Dose in Initial Clinical Trials for Therapeutics in Adult Healthy Volunteers," U.S. Department of Health and Human Research, Food and Drug Administration Center for Drug Evaluation and Research (Jul. 2005).
"M3(R2) Nonclinical Safety Studies for the Conduct of Human Clinical Trials and Marketing Authorization for Pharmaceuticals," U.S. Department of Health and Human Research, Food and Drug Administration Center for Drug Evaluation and Research, Center for Biologies Evaluation and Research (2010).
Parenti, F. et al., "Proposal to Name the Vancomycin-Ristocetin Like Glycopeptides as Dalbaheptides," The Journal of Antibiotics, (1989), 42(12):1882-1883.
Kang, et al., "Glycopeptide Antibiotics: Structure and Mechanisms of Action," Journal of Bacteriology and Virology (2015), 45(2):67-78.
Ginocchio, C., "Role of NCCLS in antimicrobial susceptibility testing and monitoring," American Journal of Health-System Pharmacy (2002), 59(S. 3).
Daabees, T. et al., "Portal and Vena Caval Plasma Methionine Concentrations in Young Pigs Administered NALM and NADM," American Journal of Nutrition (1984), 114:1541-1547.
Friedmann, M., et al., "Nutritional Value and Safety of Methionine Derivatives, Isomeric Dipeptides and Hydroxy Analogs in Mice.", Amerian Institute of Nutrition, (1988), 118:388-397.
Boggs, R., et al., "Acetylmethionine as a Source of Methionine in the Rat," American Journal of Nutrition (1975), 105:326-330.
Rotruck, J., et al., "Comparative Metabolism of L-Methionine and N-Acetylated Derivatives of Methionine," American Journal of Nutrition (1975), 105(3):331-337.
Baker, D.H., "Efficacy of the D- and L-isomers of N-Acetylmethionine for Chicks Fed Diets Containing Either Crystalline Amino Acids or Intact Protein," American Journal of Nutrition (1979), 109(6):970-974.
Cho, E., et al., "D-Methionine Utilization During Parenteral Nutrition in Rats," American Journal of Nutrition (1979), 109(6):1086-1993.
Center for Drug Evaluation and Research, Approved Package for Application No. 211962Orig1s000 for Xellia Pharmaceuticals, ApS, Vancomycin Injection, Feb. 15, 2019.

* cited by examiner

*Primary Examiner* — Sudhakar Katakam
*Assistant Examiner* — Zachary J Miknis
(74) *Attorney, Agent, or Firm* — Transformative Legal, LLC; Len S. Smith; Denise M. Brown (57) ABSTRACT

The invention relates to formulations and compositions comprising one or more glycopeptide antibodies or a pharmaceutically acceptable salt thereof for parenteral administration. In particular, stable liquid formulations and compositions comprising vancomycin or a pharmaceutically acceptable salt thereof, N-acetyl-methionine and one or more pharmaceutically acceptable excipients. The invention also relates to a process of preparing such compositions and methods and uses thereof.

24 Claims, No Drawings

GLYCOPEPTIDE ANTIBIOTICS LIQUID FORMULATIONS AND METHODS AND USES THEREOF

RELATED APPLICATIONS

This application claims the benefit of and priority in and to U.S. Provisional Application No. 63/107,919, filed Oct. 30, 2020, which is hereby incorporated by reference herein in its entirety.

FIELD

Disclosed herein are liquid formulations comprising one or more glycopeptide antibiotics or a pharmaceutically acceptable salt thereof for parenteral administration. In particular, this disclosure relates to liquid formulations comprising vancomycin or a pharmaceutically acceptable salt thereof, N-acetyl-methionine and one or more pharmaceutically acceptable excipients. This disclosure also relates to a process of preparing such compositions, methods and uses thereof.

BACKGROUND

The following includes information that may be useful in understanding the invention. It is not an admission that any of the information specifically or implicitly referenced herein is prior art, or essential, to the described or claimed invention. All references, including, but not limited to, patents, patent applications, non-patent references, and products, mentioned herein and their respective disclosures are hereby incorporated by reference herein in their entirety.

Glycopeptide antibiotics are a class of naturally occurring or semi-synthetic antimicrobial agents which act by inhibition of bacterial cell wall biosynthesis and/or membrane integrity. The glycopeptide antibiotics, such asvancomycin, teicoplanin, oritavancin, dalbavancin and telavancin, have potent activity against abroad range of Gram-positive organisms, including staphylococci (including methicillin-resistant *Staphylococcus aureus*), *Streptococcus* spp. and *Enterococcus* spp. Among these glycoside antibiotics, vancomycin is most widely used with strong bactericidal activity against many Gram-positive bacteria, and is useful for treatment of resistant and/or severe infections caused by susceptive strains of methicillin-resistant (beta-lactam-resistant) staphylococci.

Vancomycin is a tricyclic glycopeptide antibiotic derived from Amycolatopsis *orientalis* (formerly, *Nocardia orientalis*), and the IUPAC name is (Sa)-(3S,6R,7R,22R,23S,26S, 36R,38aR)-44-{[2-O-(3-amino-2,3,6-trideoxy-3-C-methyl-α-L-lyxo-hexopyranosyl)-β-D-glu-copyranosyl]-oxy}-3-(carbamoylmethyl)-10,19-dichloro-2,3,4,5,6,7,23,24,25,26, 36,37,38,38a-tetradecahydro-7,22,28,30,32-pentahydroxy-6-[(2R)-4-methyl-2-(methylamino] valerami-do]-2,5,24,38, 39-pentaoxo-22H-8,11:18,21-dietheno-23,36(iminometh-ano)-13,16: 31,35-di-metheno-1H,16H-[1,6,9]-oxadiazacy-clohexadecino-[4,5-m][10,2,16]-benzoxadiazacyclotet-ra-cosine-26-carboxylic acid.

Vancomycin hydrochloride is indicated for the treatment of serious or severe infections caused by susceptible strains of methicillin-resistant (beta-lactam-resistant) staphylococci. It is indicated for penicillin-allergic patients, for patients who cannot receive or who have failed to respond to other drugs, including the penicillins or cephalosporins, and for infections caused by vancomycin-susceptible organisms that are resistant to other antimicrobial drugs. Related glycopeptide antibiotics, such as teicoplanin and telavancin, are also used for the treatment of multi-drug resistant gram-positive bacterial infections.

In pharmaceutical use, Vancomycin is usually administered as the hydrochloride salt, Vancomycin hydrochloride, represented by the following structural formula:

Vancomycin is approved and marketed in the form of capsule and intravenous injection, wherein the injection products are supplied as a lyophilized powder or as a frozen solution. Lyophilized powder, prior to administration to a patient, can be reconstituted with water for injection and further diluted in an intravenous bag with like saline or dextrose solution. The stability of reconstituted solutions and diluted solutions, is limited under refrigerated conditions. Other disadvantages of diluted formulations include that the pH of the diluted formulation can vary depending on the choice of the diluent. The dilution step can also present contamination issues, dosage errors, and thus safety hazards for the patient. Prior to the patient administration, frozen vancomycin solutions undergo long and cumbersome processes which include thawing at room temperature or under refrigeration, which impedes quick application for clinical use. In addition, a thawed vancomycin solution is chemically stable for only 72 hours at room temperature or for 30 days when stored under refrigerated conditions.

In the field of injectable preparations, attempts have been performed to stabilize vancomycin and related glycopeptide antibiotics.

U.S. Pat. No. 4,670,258A discloses protection of vancomycin against thermal degradation by mixing certain acetylated dipeptides or tripeptides with vancomycin in solution in a narrow molar ratio of 1 to 2 moles of peptide to Vancomycin.

U.S. Pat. No. 4,885,275A discloses gel-free concentrated aqueous formulations of vancomycin hydrochloride are provided which comprise the antibiotic salt at a concentration between about 12% and about 50% w/v and a gel-inhibiting compound, e.g., ethanol, at a concentration between about 1% and about 20% v/v.

U.S. Pat. No. 8,778,873B2 discloses a pharmaceutical composition containing two different antibiotics, a glycopeptide and a cephalosporin, combined with the help of at least one solubilizing/stabilizing agent such as sodium bicarbonate or L-arginine.

U.S. Patent Application Publication No. 2014/0260098A1 discloses a method for a preparation of spray dried vancomycin hydrochloride powder, wherein excipients selected from stabilizers; solubilizers; a saccharide; a polyol; polyethylene glycol 400; and surfactants are added.

PCT International Application Publication No. WO1997/019690A1 discloses solutions of vancomycin hydrochloride comprising about 0.5% and about 30% v/v ethanol.

PCT International Application Publication No. WO2001/82971A2 discloses pharmaceutical compositions containing a cyclodextrin and a therapeutically effective amount of a glycopeptide antibiotic or a salt thereof.

PCT International Application Publication No. WO 2014/085526A1 discloses lipid-based vancomycin composition, wherein the composition comprises a lipid component, a glycopeptide antibiotic, and an amino acid or a derivative thereof.

European Patent No. EP 1,278,549B1 discloses a pharmaceutical composition comprising a cyclodextrin and a group of glycopeptide antibiotics. The examples involve Telavancin and hydroxy propyl-β-cyclodextrins or sulfobutylether-γ-cyclodextrins.

Japanese Patent No. JP 11,080,021 discloses vancomycin injection suppressed in discoloration, comprising water, Vancomycin and 0.1 wt % to 10 wt % amino acids (i.e., Glycine).

Japanese Patent Application Publication No. JP 2008201778A discloses aqueous vancomycin preparations with addition of glycerol and D-alanine or DL-alanine and/or D-lactic acid or DL-lactic acid.

In 2019, the United States Food and Drug Administration (FDA) approved Vancomycin Hydrochloride injection for intravenous administration (VANCO READY™) developed by Xellia Pharmaceuticals APS for the treatment of (1) Septicemia, (2) Infective Endocarditis, (3) Skin and Skin Structure Infections, (4) Bone Infections and (5) Lower Respiratory Tract Infections. The products are available in single-dose flexible bags, are sterile nonpyrogenic premixed 100 mL, 150 mL, 200 mL, 250 mL, 300 mL, 350 mL or 400 mL solutions containing 500 mg, 750 mg, 1 gram, 1.25 grams, 1.5 grams, 1.75 grams or 2 grams vancomycin, respectively, as vancomycin hydrochloride. Each 100 mL of solution contains 1.8 mL polyethylene glycol 400, 1.36 grams N-acetyl-D-alanine, 1.26 grams L-lysine hydrochloride (monochloride) in water for injection. Hydrochloric acid and sodium hydroxide are used for pH adjustment. The pH is 4.5 to 5.5 and the osmolarity is 350 mOsmol/L to 475 mOsmol/L. However, VANCO READY™'s product label contains a black box warning for risk of embryo-fetal toxicity due to excipients, stating that "this formulation of vancomycin injection, USP is not recommended for use during pregnancy because it contains the excipients polyethylene glycol (PEG 400) and N-acetyl D-alanine (NADA), which caused fetal malformations in animal reproduction studies. If use of vancomycin is needed during pregnancy, use other available formulations of vancomycin," and thus, deterring at least women and pregnant women from using the VANCO READY™'s product.

Additionally, the Vancomycin composition VANCO READY™ and its use are described in U.S. Pat. Nos. 10,039,804 and 10,188,697, and include stable Vancomycin antibiotic pharmaceutical compositions using as N-acetyl-D-alanine and/or N-acetyl-glycine in the formulation. The use of N-acetyl-D-alanine and/or N-acetyl-glycine in Vancomycin antibiotic formulations provides stable solutions. However, substituting N-acetyl-D-alanine and/or N-acetyl-glycine for other excipients, for example, N-acetylated dipeptides or tripeptides, causes the preparation to became hazy or leads to rapid degradation of vancomycin and thus such preparations are not stable or suitable for use as a pharmaceutical solution in a clinical setting.

In light of the above, there is a need for improved glycopeptide antibiotic-related pharmaceutical compositions for intravenous administration which exhibit improved stability, solubility and/or efficacy, with fewer side effects, including a decreased risk of embryo-fetal toxicity in pregnant women.

SUMMARY

The inventions described and claimed herein have many attributes and aspects including, but not limited to, those set forth or described or referenced in this Summary. It is not intended to be all-inclusive and the inventions described and claimed herein are not limited to or by the features or embodiments identified in this Summary, which is included for purposes of illustration only and not restriction.

The invention provides for a stable formulation comprising one or more glycopeptide antibiotics or a pharmaceutically acceptable salt thereof for parenteral administration. Particularly, the invention provides for a liquid formulation comprising vancomycin or a pharmaceutically acceptable salt thereof, N-acetyl-methionine and one or more pharmaceutically acceptable excipients.

In some aspects, a composition comprising a glycopeptide antibiotic or a pharmaceutically acceptable salt thereof for parenteral administration, which can be intramuscular injection, subcutaneous injection, intravenous injection, and intradermal injection.

In some aspects, the formulation comprises a glycopeptide antibiotic or a pharmaceutically acceptable salt thereof in a parenteral composition, wherein the glycopeptide antibiotic is, for example, vancomycin, teicoplanin, ramoplanin, complestatin, corbomycin, bleomycin, oritavancin, dalbavancin or telavancin.

In some aspects, this disclosure provides for a liquid composition for parenteral administration comprising a glycopeptide antibiotic or a pharmaceutically acceptable salt thereof in an amount of about 0.1% by weight to about 1.0% by weight, N-acetyl-methionine in an amount of about 0.1% by weight to about 5.0% by weight, and one or more pharmaceutically acceptable excipients.

In some aspects, the one or more pharmaceutically acceptable excipients can be, for example, one or more buffers or buffering agents, one or more chelating agent, one or more tonicity agents, one or more pH adjusting agents, one or more antioxidants, one or more preservatives, water or a combination thereof. In some aspects, the one or more tonicity agents is sodium chloride.

In some aspects, the glycopeptide antibiotics or a pharmaceutically acceptable salt thereof is vancomycin hydrochloride. In some aspects, the concentration of vancomycin hydrochloride is about 5.0 mg/mL. In some aspects, the N-acetyl-methionine is N-acetyl-D-methionine or N-acetyl-L-methionine. In some aspects, the concentration of N-acetyl-D-methionine is about 15 mg/mL to about 25 mg/mL. In some aspects, the ratio of vancomycin hydrochloride to N-acetyl-D-methionine present in the composition is about 1:1 by weight to about 1:10 by weight. In some aspects, the ratio of vancomycin hydrochloride to N-acetyl-D-methionine present in the composition is about 1:5 by molar to 1:50 by molar.

In some aspects, the formulation does not include N-acetyl D-alanine, polyethylene glycol-400, or both N-acetyl D-alanine and polyethylene glycol-400.

In some aspects, the formulation is an aqueous solution. In some aspects, the formulation has a pH of about 2 to about 7, preferably about 5.0 adjusted with hydrochloric acid solutions or sodium hydroxide.

In some aspects, the formulation is a ready-to-use solution for intravenous, subcutaneous or intramuscular administration.

In some aspects, this disclosure provides for a liquid composition comprising:
vancomycin hydrochloride in an amount of about 0.5% by weight,
N-acetyl-D-methionine in an amount of about 1.5% to about 2.5% by weight,
sodium chloride in an amount of about 0.012% by weight,
sodium hydroxide or hydrochloride to adjust the composition pH of about 5.0, and water.

In some aspects, this disclosure provides for a liquid composition filled in a vial, an ampoule, a bag, a bottle, a cartridge, or a syringe.

In some aspects, the liquid composition contains about 2.5% or less of total impurities.

In some aspects, the liquid composition is stable for at least about 3 months at 25±2° C.

In some aspects, this disclosure provides for a process for preparation of a liquid composition for parenteral administration which comprises:
one or more glycopeptide antibiotics or a pharmaceutically acceptable salt thereof in an amount of about 0.1% by weight to about 1.0% by weight,
N-acetyl-D-methionine in an amount of about 1.5% to about 2.5% by weight,
sodium chloride in an amount of about 0.012% by weight,
sodium hydroxide or hydrochloride to adjust the composition pH of about 5.0, and
water,
wherein the process comprises a step of sterilizing the liquid composition by one or more methods is heat sterilization, gaseous sterilization, filtration sterilization, radiation sterilization, or a combination thereof.

In some aspects, this disclosure provides for a method for treating one or more bacterial infections or one or more bacterial infection-related conditions in a subject in need thereof, the method comprising administering to the subject a liquid formulation that comprises:
a therapeutically effective amount of one or more glycopeptide antibiotics or a pharmaceutically acceptable salt thereof,
N-acetyl-methionine (such as N-acetyl-D-methionine, N-acetyl-L-methionine, or a combination thereof), and
one or more pharmaceutically acceptable excipients,
wherein the liquid formulation does not include N-acetyl D-alanine or polyethylene glycol-400 or both N-acetyl D-alanine and polyethylene glycol-400.

In some aspects, the subject is male, female, pregnant female, adult, child, mammal, human, or a combination thereof.

In some aspects, the one or more bacterial infections is one or more skin and/or skin structure infections, one or more bone infections, one or more lower respiratory tract infections, or a combination thereof. In some aspects, the one or more bacterial infection-related conditions is septicemia, infective endocarditis, or a combination thereof.

In some aspects, this disclosure provides for a method of treating one or more bacterial infections or one or more bacterial infection-related conditions in a subject in need thereof, the method comprising administering to the subject a liquid formulation that comprises:
(a) a therapeutically effective amount of one or more glycopeptide antibiotics or a pharmaceutically acceptable salt thereof,
(b) N-acetyl-methionine and
(c) one or more pharmaceutically acceptable excipients,
wherein the liquid formulation does not include N-acetyl D-alanine or polyethylene glycol-400 or both N-acetyl D-alanine and polyethylene glycol-400.

In some aspects, this disclosure provides for a method of treating an infectious disease in a subject in need thereof, the method comprising administering to the subject a liquid formulation that comprises:
(a) a therapeutically effective amount of one or more glycopeptide antibiotics or a pharmaceutically acceptable salt thereof,
(b) N-acetyl-methionine, and
(c) one or more pharmaceutically acceptable excipients,
wherein the liquid formulation does not include N-acetyl D-alanine or polyethylene glycol-400 or both N-acetyl D-alanine and polyethylene glycol-400.

In some aspects, the infectious disease is caused by Methicillin-resistant *Staphylococcus aureus* (MRSA), enterococci, vancomycin-resistant enterococci (VRE), coagulase negative staphylococci, or a combination thereof.

In some aspects, this disclosure provides for a method of treating a subject suffering from an infection caused by Gram-positive organisms, the method comprising administering to the subject in need thereof a liquid formulation that comprises:
(a) a therapeutically effective amount of one or more glycopeptide antibiotics or a pharmaceutically acceptable salt thereof,
(b) N-acetyl-methionine, and
(c) one or more pharmaceutically acceptable excipients,
wherein the liquid formulation does not include N-acetyl D-alanine or polyethylene glycol-400 or both N-acetyl D-alanine and polyethylene glycol-400.

In some aspects, the Gram-positive organisms is *Staphylococcus, Streptococcus* spp., *Enterococcus* spp. or a combination thereof. In some aspects, the infection caused by Gram-positive organisms is a staphylococcal infection. In some aspects, the staphylococcal infection is staphylococcal endocarditis, staphylococcal septicemia, or a combination thereof.

In some aspects, this disclosure provides for a method of treating a subject suffering from an inflammatory disease, the method comprising administering to the subject in need thereof a liquid formulation that comprises:
  (a) a therapeutically effective amount of one or more glycopeptide antibiotics or a pharmaceutically acceptable salt thereof,
  (b) N-acetyl-methionine, and
  (c) one or more pharmaceutically acceptable excipients, wherein the liquid formulation does not include N-acetyl D-alanine or polyethylene glycol-400 or both N-acetyl D-alanine and polyethylene glycol-400.

In some aspects, the inflammatory disease is enterocolitis, rheumatic fever, endocarditis, colitis, or a combination thereof.

In some aspects, the liquid composition administered to the subject in need thereof comprises:
  one or more glycopeptide antibiotics or a pharmaceutically acceptable salt thereof in an amount of about 0.1% by weight to about 1.0% by weight of the composition,
  wherein the weight ratio of glycopeptide antibiotics or the pharmaceutically acceptable salt thereof to N-acetyl-methionine (such as N-acetyl-D-methionine, N-acetyl-L-methionine, or a combination thereof) present in the composition is about 1:1 by weight to about 1:100 by weight, 1:1 by weight to about 1:50 by weight, or 1:1 by weight to 1:10 by weight In some aspects, a liquid composition administered to a subject in need thereof comprises:
  one or more glycopeptide antibiotics or a pharmaceutically acceptable salt thereof, and
  N-acetyl-methionine;
  wherein the molar ratio of glycopeptide antibiotics or the pharmaceutically acceptable salt thereof to the N-acetyl-methionine (such as N-acetyl-D-methionine, N-acetyl-L-methionine, or a combination thereof) present in the liquid composition is about 1:5 by molar to about 1:50 by molar.

In some aspects, the one or more glycopeptide antibiotics or a pharmaceutically acceptable salt thereof in the liquid composition administered to a subject in need thereof is vancomycin.

In some aspects, the maximum daily intake (MDI) of N-acetyl-D-methionine is 10 grams/day based on a 100 mL drug product bag containing 0.5 grams vancomycin and 2.5 grams N-acetyl-D-methionine.

In some aspects, the one or more one or more glycopeptide antibiotics or a pharmaceutically acceptable salt thereof is vancomycin, the maximum daily dose (MDD) of vancomycin is 2 grams/day for 10 days or less.

In some aspects, this disclosure provides for a process for preparing a liquid composition for parenteral administration, the process comprising:
  (a) adding a glycopeptide or pharmaceutically acceptable salt to sterilized water;
  (b) stirring the solution until the glycopeptide or pharmaceutically acceptable salt is fully dissolved by visual inspection;
  (c) adding N-acetyl-D-methionine (NADM) to the solution and stirring until the NADM is fully dissolved by visual inspection;
  (d) adding sodium chloride and stirring until the components of the solution are fully dissolved by visual inspection;
  (e) adjusting the pH to about 5.0 using Hydrochloric acid or sodium hydroxide;
  (f) QS with sterilized water suitable for injection to a selected total volume; and
  (g) stirring for an additional selected amount of time to form a prepared composition.

In some aspects, the sterilized water is prepared by one or more of heat sterilization, gaseous sterilization, filtration sterilization, or radiation sterilization.

In some aspects, the preparation process can further comprise the step of:
  (h) aseptically filling the prepared solution into sterile bags of appropriate size In some aspects, the relative amount of the one or more glycopeptide antibiotics or a pharmaceutically acceptable salt thereof in the prepared composition is about 0.1% by weight to about 1.0% by weight.

In some aspects, the relative amount of the N-acetyl-methionine in the prepared composition is about 1.5% to about 2.5% by weight.

In some aspects, the relative amount of the sodium chloride in the prepared solution is about 0.012% by weight.

DETAILED DESCRIPTION

Vancomycin and related glycopeptide parenteral formulations which exhibit a safe and effective use of vancomycin to the entire treatment spectrum including the use of vancomycin during pregnancy are an unmet need. The inventors have determined that there is an enduring need to develop vancomycin formulation that can provides an alternative to existing formulations, and which remain stable and soluble in solution over extended periods of time to allow for clinical utility. The inventors have surprisingly found that by use of N-acetyl-methionine (such as N-acetyl-D-methionine, N-acetyl-L-methionine, or a combination thereof) in the formulations provide stable vancomycin formulations which remain suitable for administration to a subject throughout the product shelf life, can be used in treating one or more bacterial infections in the subject, and can be used during pregnancy.

N-acetyl-methionine is a chiral molecule with D (NADM) and L (NALM) forms, consistent with the D and L forms of methionine. NADM is used in nonclinical research as a preservative/stabilizer. The NALM form is used widely in food and medicine as a stable chemical precursor and as the alternative form of the essential amino acid L-methionine.

The toxicity of NADM and NALM appears to suggest that NADM is less toxic than NALM and is therefore a suitable component of vancomycin compositions. NADM in orally-dosed pigs (~382 milligrams/kilogram body weight [mg/kg]), appeared rapidly in the plasma (peak plasma concentration achieved 15 minutes after dosing), with NADM only minimally hydrolyzed to D- and L-methionine and thought to be excreted mostly intact in the urine (Daabees, T. et al., "Portal and vena caval plasma methionine concentrations in young pigs administered L-methionine, NALM and NADM," J. Nutrition, 114:1541-1547 (1984) (Daabees 1984); Friedmann, M. et al., "Nutritional value and safety of methionine derivatives, isomeric dipeptides and hydroxy analogs in mice," J. Nutrition, 118:388-397 (1988) (Friedmann 1988). This pathway has been confirmed by other studies where orally or intraperitoneally-(IP) dosed NADM in rodents was not a significant source of either D- or L-methionine (Boggs, R. et al., "Acetylmethionine as a source of methionine in the rat," J. Nutrition, 105:326-330 (1975) (Boggs 1975); Rotruck, J. et al., "Comparative metabolism of L-methionine and N-acetylated derivatives of methionine," J. Nutrition, 105(3):331-337 (1975) (Rotruck 1975); Baker, D. H., "Efficacy of the D- and L-isomers of N-acetylmethionine for chicks fed diets containing either crystalline amino acids or intact protein," J. Nutrition, 109(6):970-974 (1979) (Baker 1979)). In rodents and pigs some low levels of L-methionine may be produced from D-methionine (Cho, E. et al., "D-methionine utilization during parenteral nutrition in rats," J. Nutrition, 109(6): 1086-1093 (1979) (Cho 1979)). Primates, however, are not able to convert D-methionine to the active form of L-methionine; therefore, an oral human dose of NADM would not produce L-methionine. However, NALM, unlike NADM, is absorbed rapidly and is completely hydrolyzed to L-methionine and acetic acid (and ultimately to carbon dioxide) via the action of acylases (Daabees 1984; Friedman 1988; Baker 1979; European Food Safety Agency (EFSA). 2003. NALM for use in foods for special medical purposes. EFSA Journal. 22:1-10 (EFSA 2003)). Subsequently, L-methionine is utilized as an essential amino acid in various biochemical processes (Rotruck 1975). While no acute lethal studies have been performed with NADM directly, it is known that NALM has an LD50 (rats, IV) of 435 mg/kg, and N-acetyl-DL-methionine has an LD50 (rats, IP) of 6700 mg/kg. The significant difference between the racemate (which comprises 50/50 NADM and NALM) and NALM alone suggests that NADM is less toxic than NALM and would therefore be a suitable component of a vancomycin composition for IP administration.

In some embodiments, this disclosure provides for a stable formulation or pharmaceutical composition comprising one or more glycopeptide antibiotics or a pharmaceutically acceptable salt thereof for parenteral administration. In particular, the invention provides a liquid formulation comprising vancomycin or a pharmaceutically acceptable salt thereof, N-acetyl-methionine (such as N-acetyl-D-methionine, N-acetyl-L-methionine, or a combination thereof), and one or more pharmaceutically acceptable excipients.

In some embodiments, a formulation or composition comprising one or more glycopeptide antibiotics or a pharmaceutically acceptable salt thereof and N-acetyl-methionine (such as N-acetyl-D-methionine, N-acetyl-L-methionine, or a combination thereof). In some embodiments, the composition may be in the form of a ready-to-use liquid formulation. In some embodiments, the formulation or composition is aqueous.

In some embodiments, the N-acetyl-methionine used in the formulation or composition may be in the form of D or L isomers (N-acetyl-D-methionine or N-acetyl-L-methionine), or both.

In some embodiments, the weight ratio of one or more glycopeptide antibiotics or a pharmaceutically acceptable salt thereof to N-acetyl-methionine (such as N-acetyl-D-methionine, N-acetyl-L-methionine, or a combination thereof) present in the formulation or composition may be about 1:1 by weight to about 1:100 by weight, 1:1 by weight to about 1:50 by weight, or 1:1 by weight to 1:10 by weight. In some embodiments, weight ratio of one or more glycopeptide antibiotics or a pharmaceutically acceptable salt thereof to N-acetyl-methionine (such as N-acetyl-D-methionine, N-acetyl-L-methionine, or a combination thereof) present in the formulation or composition may be about 1:3 by weight to about 1:5 by weight. In some embodiments, the molar ratio of one or more glycopeptide antibiotics or a pharmaceutically acceptable salt thereof to N-acetyl-methionine (such as N-acetyl-D-methionine, N-acetyl-L-methionine, or a combination thereof) present in the formulation or composition may be about 1:5 by molar to about 1:50 by molar, or about 1:5 by molar, about 1:6 by molar, about 1:7 by molar, about 1:8 by molar, about 1:9 by molar, about 1:10 by molar, about 1:11 by molar, about 1:12 by molar, about 1:13 by molar, about 1:14 by molar, about 1:15 by molar, about 1:16 by molar, about 1:17 by molar, about 1:18 by molar, about 1:19 by molar, about 1:20 by molar, about 1:21 by molar, about 1:22 by molar, about 1:23 by molar, about 1:24 by molar, about 1:25 by molar, about 1:26 by molar, about 1:27 by molar, about 1:28 by molar, about 1:29 by molar, about 1:30 by molar, about 1:31 by molar, about 1:32 by molar, about 1:33 by molar, about 1:34 by molar, about 1:35 by molar, about 1:36 by molar, about 1:37 by molar, about 1:38 by molar, about 1:39 by molar, about 1:40 by molar, about 1:41 by molar, about 1:42 by molar, about 1:43 by molar, about 1:44 by molar, about 1:45 by molar, about 1:46 by molar, about 1:47 by molar, about 1:48 by molar, about 1:49 by molar, or about 1:50 by molar.

In some embodiments, the formulation or composition comprises one or more glycopeptide antibiotics or a pharmaceutically acceptable salt thereof and N-acetyl-methionine (such as N-acetyl-D-methionine, N-acetyl-L-methionine, or a combination thereof), wherein the formulation or composition does not include N-acetyl D-alanine, or polyethylene glycol-400 or both N-acetyl D-alanine and polyethylene glycol-400.

In some embodiments, the formulation or composition comprises one or more glycopeptide antibiotics or a pharmaceutically acceptable salt thereof and N-acetyl-methionine (such as N-acetyl-D-methionine, N-acetyl-L-methionine, or a combination thereof) and one or more amino acids. In some embodiments, the one or more amino acids is glycine, alanine, serine, leucine, valine, lysine, arginine, ornithine, in the forms of L-form and/or D-form, or a combination thereof.

In some embodiments, the formulation or composition comprises one or more glycopeptide antibiotics or a pharmaceutically acceptable salt thereof and N-acetyl-methionine (such as N-acetyl-D-methionine, N-acetyl-L-methionine, or a combination thereof), wherein the formulation or composition is devoid of an amino acid.

In some embodiments, the formulation or composition comprises one or more glycopeptide antibiotics or a pharmaceutically acceptable salt thereof in an amount of about 0.1% by weight to about 1.0% by weight.

In some embodiments, the formulation or composition comprise N-acetyl-methionine (such as N-acetyl-D-methionine, N-acetyl-L-methionine, or a combination thereof) in an amount of about 0.1% by weight to about 5.0% by weight.

In some embodiments, the formulation or composition is in the form of a solution, a suspension or a dispersion.

In some embodiments, the formulation or composition has a pH of about 2 to about 7, preferably about 5.0 adjusted with one or more hydrochloric acid solutions or one or more sodium hydroxide solutions.

In some embodiments, the formulation or composition is preferably aqueous and typically may include about 50%, about 60%, about 70%, about 80%, about 85%, about 90%, about 95%, about 98% or about 99% by weight water.

In some embodiments, suitable diluents for the disclosed formulation and compositions herein include any known diluent acceptable for pharmaceutical use (example, intravenous administration); for example, water, physiological saline, 5% dextrose solution, lactated Ringer's solution, or a combination thereof.

In some embodiments, the formulation or composition may be suitable for storage in vials, syringes or infusion containers, such as, for example, bottles, infusion bags or the like, and may show chemical and physical stability when stored at temperatures from about 2° C. to about 30° C.

In some embodiments, the formulation or composition comprise N-acetyl-methionine (such as N-acetyl-D-methionine, N-acetyl-L-methionine, or a combination thereof), and further comprise one or more pharmaceutically acceptable excipients, the one or more pharmaceutically acceptable excipients is one or more tonicity agents, one or more preservatives, one or more surfactants, one or more buffering agents, one or more pH-adjusting agents, one or more vehicles, or a combination thereof.

In some embodiments, the formulation or composition retains at least about 90% w/w of the potency of the one or more glycopeptide antibiotics or a pharmaceutically acceptable salt thereof when stored at about 25° C. and about 60% relative humidity or at about 40° C. and about 75% relative humidity for about 3 months.

In some embodiments, the formulation or composition exhibits stability throughout the shelf life as the impurities observed are well below the specified limits, and the stability may be an improvement from VANCO READY™'s stability. Stability of the formulation or composition can be expressed as the amount of glycopeptide antibiotic, for example, vancomycin, impurities present after a predetermined time period.

In some embodiments, a stable liquid formulations comprising vancomycin or a pharmaceutically acceptable salt thereof, N-acetyl-methionine (such as N-acetyl-D-methionine, N-acetyl-L-methionine, or a combination thereof) and one or more pharmaceutically acceptable excipients.

In some embodiments, a liquid formulation comprising vancomycin or a pharmaceutically acceptable salt thereof, N-acetyl-methionine (such as N-acetyl-D-methionine, N-acetyl-L-methionine, or a combination thereof) and one or more pharmaceutically acceptable excipients, wherein the liquid formulation is devoid of N-acetyl D-alanine or polyethylene glycol-400 or both.

In some embodiments, there is provided premixed ready-to-use injectable compositions of one or more glycopeptide antibiotics or a pharmaceutically acceptable salt thereof, N-acetyl-methionine (such as N-acetyl-D-methionine, N-acetyl-L-methionine, or a combination thereof) and one or more pharmaceutically acceptable excipients, to avoid the inconvenience of diluting a concentrated small volume parenteral formulation into infusion diluents prior to infusion, and to eliminate the risk of microbiological contamination during aseptic handling and any potential calculation or dilution error.

In some embodiments, a stable ready-to-use liquid formulation comprising vancomycin hydrochloride in an amount of about 0.1% by weight to about 1.0% by weight, N-acetyl-methionine (such as N-acetyl-D-methionine, N-acetyl-L-methionine, or a combination thereof) in an amount of about 0.1% by weight to about 5.0% by weight, sodium chloride in an amount of about 0.005% by weight to about 0.05% by weight, sodium hydroxide or hydrochloride to adjust the composition pH of about 5.0, and water for injection.

In some embodiments, a stable ready-to-use liquid formulation comprising vancomycin hydrochloride in an amount of about 0.51% by weight, N-acetyl-D-methionine in an amount of about 2.5% by weight, sodium chloride in an amount of about 0.012% by weight, sodium hydroxide or hydrochloride to adjust the composition pH of about 5.0, and water for injection.

In some embodiments, a stable liquid formulation comprising vancomycin hydrochloride in an amount of about 0.51% by weight, N-acetyl-D-methionine in an amount of about 1.5% by weight, sodium chloride in an amount of about 0.012% by weight, sodium hydroxide or hydrochloride to adjust the composition pH of about 5.0, and water for injection.

In some embodiments, a stable liquid formulation comprising vancomycin or a pharmaceutically acceptable salt thereof, N-acetyl-D-methionine and one or more pharmaceutically acceptable excipients, wherein the obtained formulation exhibits stability throughout the shelf life as the impurities observed are well below the specified limits. Such stability may be an improvement relative to VANCO READY™'s stability.

In some embodiments, a process for preparing a liquid formulation comprising vancomycin or a pharmaceutically acceptable salt thereof, N-acetyl-methionine (such as N-acetyl-D-methionine, N-acetyl-L-methionine, or a combination thereof) and one or more pharmaceutically acceptable excipients.

In some embodiments, the process for preparing and sterilizing the liquid formulation may provide a reduction in the amount of related compounds and impurities associated with the formulations on storage.

In some embodiments, the sterilization is carried out by using one or more methods, such methods include, but are not limited to, heat sterilization, gaseous sterilization, filtration sterilization, radiation sterilization, or a combination thereof.

In some embodiments, a method for treating one or more bacterial infections in a subject in need thereof, the method comprising administering to the subject a liquid formulation comprising a therapeutically effective amount of one or more glycopeptide antibiotics or a pharmaceutically acceptable salt thereof, N-acetyl-methionine (such as N-acetyl-D-methionine, N-acetyl-L-methionine, or a combination thereof) and one or more pharmaceutically acceptable excipients.

In some embodiments, a method for treating one or more bacterial infections in a subject in need thereof, the method comprising administering to the subject a liquid formulation comprising a therapeutically effective amount of one or more glycopeptide antibiotics or a pharmaceutically acceptable salt thereof, N-acetyl-methionine (such as N-acetyl-D-methionine, N-acetyl-L-methionine, or a combination thereof) and one or more pharmaceutically acceptable excipients, wherein the composition is devoid of N-acetyl D-alanine or polyethylene glycol-400 or both.

In some embodiments, the subject is male, female, pregnant female, adult, child, mammal, human, or a combination thereof.

In some embodiments, the one or more bacterial infections is one or more skin and/or skin structure infections, one or more bone infections, one or more lower respiratory tract infections, or a combination thereof. In some aspects, the one or more bacterial infection-related conditions is septicemia, infective endocarditis, or a combination thereof.

In some embodiments, the maximum daily intake (MDI) of N-acetyl-D-methionine is 10 grams/day based on a 100 mL drug product bag containing 0.5 grams vancomycin and 2.5 grams N-acetyl-D-methionine.

In some embodiments, the one or more one or more glycopeptide antibiotics or a pharmaceutically acceptable salt thereof is vancomycin, the maximum daily dose (MDD) of vancomycin is 2 grams/day for 10 days or less.

Definitions

General terms used in formula can be defined as follows; however, the meaning stated should not be interpreted as limiting the scope of the term per se.

As used herein, the recitation of a numerical range for a variable is intended to convey that the invention may be practiced with the variable equal to any of the values within that range. Thus, for a variable that is inherently discrete, the variable can be equal to any integer value of the numerical range, including the end-points of the range. Similarly, for a variable, which is inherently continuous, the variable can be equal to any real value of the numerical range, including the end-points of the range. As an example, a variable which is described as having values between 0 and 2, can be 0, 1 or 2 for variables which are inherently discrete, and can be 0.0, 0.1, 0.01, 0.001, or any other real value, for variables which are inherently continuous.

Figure 1:
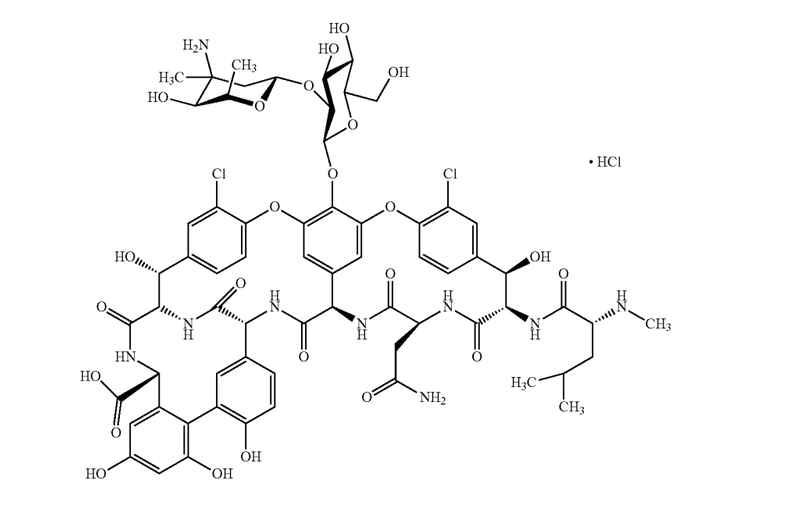

As used herein, the term "glycopeptide antibiotics" refers to molecules which contain a heptapeptide structure providing specific affinity for the D-alanyl-D-Alanine terminus of the peptidoglycan pentapeptide including, for example, vancomycin, telavancin, oritavancin, teicoplanin and dalbavancin (See, e.g., Parenti & Cavalleri, "Proposal to Name the Vancomycin-Ristocetin Like Glycopeptides as Dalbaheptides," J. Antibiotics, 4(12):1882 (December 1989)). Structures for some of those molecules are shown in FIG. 1, which is adapted from Kang, H-K. et al., "Glycopeptide Antibiotics: Structure and Mechanisms of Action," J. Bacteriol. Virol., 45(2):67-78 (2015).

As used herein, the term "vancomycin" refers to not only vancomycin per se, but also its other pharmaceutically acceptable salts, pharmaceutically acceptable solvates, pharmaceutically acceptable hydrates, pharmaceutically acceptable enantiomers, pharmaceutically acceptable derivatives, pharmaceutically acceptable polymorphs and pharmaceutically acceptable prodrugs thereof. The formulations of the invention preferably comprise vancomycin hydrochloride.

As used herein, the term "Methionine" refers to the sulfur-containing essential amino acid that improves muscle tone and elasticity of the skin, hair and strengthens nails. It is one of the nine essential amino acids in humans. L-Methionine is the natural-occurring amino acid. D-methionine may be eliminated unchanged in urine or feces.

As used herein, the term "D-alanine" is a non-essential amino acid in humans, is used for protein construction, and is involved in the metabolism of tryptophan and vitamin pyridoxine. D-Alanine is the non-proteinogenic form of alanine which is used in bacterial cell wall biosynthesis, and helps in the metabolism of sugars and organic acids.

As used herein, the term "N-acetyl-methionine" is a compound represented by the following structure:

N-acetyl-methionine
CAS# 1115-47-5

N-acetyl-methionine can exist as an acid or in deprotonated form. The term "N-acetyl-methionine" is also meant to cover any salt thereof, especially pharmaceutically acceptable salts. N-acetyl-methionine is a chiral molecule with D (NADM) and L (NALM) forms, consistent with the D and L forms of methionine represented by the following structure:

NADM
CAS# 1509-92-8

NALM
CAS# 65-82-7

NADM is used in nonclinical research and as a preservative/stabilizer. The NALM form is used widely in food and medicine as a stable chemical precursor and as the alternative form of the essential amino acid L methionine. N-acetyl-methionine can be N-acetyl-D-methionine, N-acetyl-L-methionine, or a combination thereof.

The compounds of the invention may have one or more chiral centers. The absolute stereochemistry at each chiral center may be 'R' or 'S'. The compounds of the invention include all diastereomers and enantiomers and mixtures thereof. Unless specifically mentioned otherwise, reference to one stereoisomer applies to any of the possible stereoisomers. Whenever the stereoisomeric composition is unspecified, it is to be understood that all possible stereoisomers are included.

As used herein, the term "stereoisomer" refers to a compound made up of the same atoms bonded by the same bonds but having different three-dimensional structures which are not interchangeable. The three-dimensional structures are called configurations. As used herein, the term "enantiomer" refers to two stereoisomers whose molecules are non-superimposable mirror images of one another. The term "chiral center" refers to a carbon atom to which four different groups are attached. As used herein, the term "diastereomers" refers to stereoisomers which are not enantiomers. The terms "racemate" or "racemic mixture" refer to a mixture of equal parts of enantiomers.

As used herein, the term "treating" or "treatment" of a state, disorder or condition includes: (a) preventing or delaying the appearance of clinical symptoms of the state, disorder or condition developing in a subject that may be afflicted with or predisposed to the state, disorder or condition but does not yet experience or display clinical or subclinical symptoms of the state, disorder or condition; (b) inhibiting the state, disorder or condition, i.e., arresting or reducing the development of the disease or at least one clinical or subclinical symptom thereof, (c) lessening the disease, disorder or condition or at least one of its clinical or subclinical symptoms or (d) relieving the disease, i.e., causing regression or amelioration of the state, disorder or condition or at least one of its clinical or subclinical symptoms.

As used herein, the terms "treat," "ameliorate," and "inhibit," and words stemming therefrom, as used herein, do not necessarily imply 100% or complete treatment, amelioration, or inhibition. Rather, there are varying degrees of treatment, amelioration, and inhibition of which one of ordinary skill in the art recognizes as having a potential benefit or therapeutic effect. In this respect, the disclosed methods can provide any amount of any level of treatment, amelioration, or inhibition of the disorder in an animal, particularly, a mammal (such as a human). For example, a disorder, including symptoms and/or conditions thereof, may be reduced by, for example, about 100%, about 90%, about 80%, about 70%, about 60%, about 50%, about 40%, about 30%, about 20%, or about 10%. Furthermore, the treatment, amelioration, or inhibition provided by the inventive method can include treatment, amelioration, or inhibition of one or more conditions or symptoms of the disorder, e.g., bacterial infection. Also, for purposes herein, "treatment," "amelioration," or "inhibition" can encompass delaying the onset of the disorder, or a symptom or condition thereof.

As used herein, the term "inhibitor" refers to a molecule that binds to an enzyme to inhibit the activity of said enzyme either partially or completely.

As used herein, the terms "patient" and "subject" are interchangeable and can be taken to mean any living organism that can be treated with the pharmaceutical compositions disclosed herein. The terms "patient: and "subject" include mammals (such as primates or humans) and other animals, such as domestic animals (e.g., household pets including cats and dogs, horses, cattle, pigs, chickens, turkeys, and sheep) and non-domestic animals (such as wildlife).

As used herein, the term "therapeutically effective amount" refers to the amount of a compound that, when administered to a subject for treating a disease, disorder or condition, is sufficient to cause the effect in the subject, which is the purpose of the administration. The "therapeutically effective amount" will vary depending on the compound, route of administration, the disease and its severity and the age, weight, physical condition and responsiveness of the subject to be treated.

As used herein, the term "formulation" is interchangeable with pharmaceutical formulation, liquid composition, liquid formulation, composition and solution and refers to preparations comprising vancomycin or a pharmaceutically acceptable salt; in a form suitable for parenteral administration to a patient or subject.

As used herein, the term "ready-to-use" refers to a liquid for parenteral administration that is not obtained by reconstituting a lyophilized product. The liquid ready-to-use solutions as per this invention are not diluted with any diluent before administration.

As used herein, the term "stable formulation" as used herein, refers to any preparation of one or more glycopeptide antibiotics or a pharmaceutically acceptable salt thereof having sufficient physical and chemical stability to allow storage at a convenient temperature, such as between about 0° C. and about 50° C., for a commercially reasonable period of time. The term "physical stability" refers to maintenance of color, dissolved oxygen level, head space oxygen level, and particulate matter and the term "chemical stability" relates to formation of drug-related impurities in terms of total impurity, single maximum individual impurity and maximum individual unknown impurity. For the purpose of the present invention chemical stability also includes maintenance of pH of the finished formulation. For pharmaceutical products, stability is required for commercially relevant times after manufacturing, such as for about 6, 12, 18, 24 or 36 months, during which a product is kept in its original packaging under specified storage condition.

As used herein, the term "shelf life" refers to the amount of time the formulations may be stored without loss of potency and/or dissolution profile. Preferably, the shelf life refers to the amount of time the formulations may be stored without a loss of more than about 2%, about 5%, about 8% or about 10% of the potency and/or dissolution.

As used herein, the term "about" is intended to qualify the numerical values which it modifies, denoting such a value as variable within a margin of error, typically the degree of uncertainty in the measurement system (e.g., pipette error). When no particular margin of error, such as a standard deviation to a mean value, is recited, the term "about" means plus or minus 10% of the numerical value of the number with which it is being used. By way of example, "about 50%" means in the range of 45% to 55%.

As used herein, the term "pH" as used herein, is the conventional measurement unit of hydrogen ion activity in a solution at room temperature (25° C.) unless other temperature is specified. A preferred pH range for the formulations of the invention is from about 2.0 to about 6.0; in particular from about 2.5 to about 5.5 and specifically from about 4.5 to about 5.5. The pH of the glycopeptide antibiotic formulations or compositions will be affected by the concentration of each of the ingredients. In some embodiments, the pH of the compositions described herein can be 4.0, 4.1, 4.2, 4.3, 4.4, 4.5, 4.6, 4.7, 4.8, 4.9, 5.0, or between any of the aforementioned values. The pH of the solutions is preferably measured at room temperature.

The pH of the glycopeptide antibiotic solutions according to the invention can be adjusted in any suitable manner by means of the addition of pH adjusting agents in an amount sufficient to maintain a pH of the compositions from about 2.0 to about 7.0, for example by addition of aqueous hydrochloric acid solutions or aqueous sodium hydroxide solutions. Such solutions can be diluted or concentrated. Thus, suitable pH adjusting agents include, but are not limited to 0.01M hydrochloric acid, 0.1 M hydrochloric acid, 1 M hydrochloric acid, 2 M hydrochloric acid, 3 M hydrochloric acid, 4 M hydrochloric acid, 5 M hydrochloric acid, 6 M hydrochloric acid, 0.01 M sodium hydroxide, 0.1 M sodium hydroxide, 1 M sodium hydroxide, 2 M sodium hydroxide, 3 M sodium hydroxide, 4 M sodium hydroxide, 5 M sodium hydroxide and 6 M sodium hydroxide. Thus, suitable pH adjusting agents include, but are not limited to 1 M hydrochloric acid and 1 M sodium hydroxide.

The buffer(s) or pH-adjusting agent(s) in the formulations or compositions are used to adjust the pH to a desirable range. Exemplary buffers include sodium hydroxide, sodium carbonate, sodium bicarbonate, potassium hydroxide, ammonium carbonate, hydrochloric acid, citric acid, lactic acid, phosphoric acid, sodium phosphate, sulfuric acid and the like.

As used herein, the term "pharmaceutically acceptable excipients" refers to an ingredient, other than an active ingredient, that can solubilize or stabilize an active ingredient. Pharmaceutically acceptable excipients can include or exclude: buffers or buffering agents, chelating agents (e.g., EDTA), tonicity agents, pH adjusting agents, antioxidants, preservatives and water.

As used herein, the term "pharmaceutically acceptable salt" refers to pharmaceutically acceptable organic, or inorganic, salts of a compound of the invention. Exemplary salts include, but are not limited to, amino acid salts, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate ("mesylate"), ethanesulfonate, benzenesulfonate, p-toluenesulfonate, and pamoate (i.e., 1,1'-methylene-bis(2-hydroxy-3-naphthoate)) salts. A pharmaceutically acceptable salt may involve the inclusion of another molecule, such as an acetate ion, a succinate ion, or other counter ion. In some embodiments, the counter ion is any organic, or inorganic, moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

As used herein, the term "disease state" refers to all disease states that are generally acknowledged in the art to be usefully treated with a broad spectrum antibacterial in general, and those disease states that have been found to be usefully treated by the specific antibacterials of this invention. Such disease states include, but are not limited to, treatment of a mammal afflicted with pathogenic bacteria, in particular staphylococci (methicillin sensitive and resistant), streptococci (penicillin sensitive and resistant), enterococci (vancomycin sensitive and resistant), and *Clostridium difficile*.

As used herein, the term "therapeutically effective amount" refers to that amount which is sufficient to effect treatment, as defined herein, when administered to a mammal in need of such treatment. The therapeutically effective amount will vary depending on the subject and disease state being treated, the severity of the affliction and the manner of administration, and may be determined routinely by one of ordinary skill in the art.

As used herein, the term "Biological effect" refers to, but is not limited to, increased affinity, increased selectivity, increased potency, increased efficacy, increased duration of action, decreased toxicity, and the like.

Compositions

The compositions of this disclosure include stable liquid formulations or compositions comprising comprises one or more glycopeptide antibiotics (such as vancomycin) or a pharmaceutically acceptable salt thereof and N-acetyl-methionine. In some embodiments, the N-acetyl-methionine is N-acetyl-D-methionine, N-acetyl-L-methionine, or a combination thereof.

The stable liquid vancomycin formulation or composition refers to a formulation or composition that retains at least about 90%, or about least about 95%, or at least about 96%, or at least about 98%, of the labelled concentration of vancomycin or pharmaceutically acceptable salt thereof after storage under typical and/or accelerated conditions.

The formulations or compositions include vancomycin or a pharmaceutically acceptable salt suitable for parenteral administration and one or more pharmaceutically acceptable excipients selected from buffers or buffering agents, chelating agent, antioxidant, tonicity agents, pH adjusting agents, preservatives and solvent, wherein the formulation contains N-acetyl-methionine (such as N-acetyl-D-methionine, N-acetyl-L-methionine, or a combination thereof).

The tonicity agents are used in liquid formulations or compositions to adjust the formulation or composition to be within the desired isotonic range. Exemplary tonicity agents include, but are not limited to, sodium chloride, potassium chloride, dextrose, glucose, glycerol, and mannitol. The tonicity agents are in the amount of about 0.01% by weight to about 0.8% by weight.

The preservatives in the liquid formulations or compositions are used to inhibit the microbial growth. Suitable preservatives include, but are not limited to, quaternary ammonium salts such as benzalkonium chloride and benzethonium chloride; hydrogen peroxide; sorbic acid; biquanides; cationic compounds such as chlorhexidine gluconate; p-hydroxybenzoates such as methyl p-hydroxybenzoate, ethyl p-hydroxybenzoate, propyl p-hydroxybenzoate and butyl p-hydroxybenzoate; alcohol compounds such as chlorobutanol and benzyl alcohol; sodium dehydroacetate; thiomersal and the like.

Chelating agents are used in the compositions to enhance preservative effectiveness by forming stable water-soluble complexes (chelates) with alkaline earth and heavy metal ions. Exemplary chelating agents include, but are not limited to, ethylenediaminetetraacetic acid (EDTA), or salts thereof. The chelating agent typically is present in an amount from about 0.001 by weight to about 0.1% by weight. In the case of EDTA, the chelating agent is preferably present at a concentration of about 0.025% by weight.

In some embodiments, the formulations and compositions of this disclosure may further comprise an amino acid. In one embodiment, the stable or stabilized glycopeptide antibiotic compositions according to the invention comprise vancomycin and include optionally an amino acid. The preferred amino acids include alanine, serine, leucine, valine, lysine, arginine and ornithine. The most preferred amino acids include D-alanine, D-serine, D-leucine, D-valine, L-lysine, D-lysine, L-ornithine, D-ornithine or L-arginine. The amino acids can be added to the formulations or compositions in the form of pharmaceutically acceptable salts.

The formulations or compositions can be prepared by using any suitable technique, many of which are known to those skilled in the art and can be combined in any order.

The ratio of the glycopeptide antibiotic to N-acetyl-methionine (such as N-acetyl-D-methionine, N-acetyl-L-methionine, or a combination thereof) can range from 1:1.2 to 1:50, inclusive thereof. In some embodiments, the ratio of glycopeptide antibiotic to N-acetyl-methionine (such as N-acetyl-D-methionine, N-acetyl-L-methionine, or a combination thereof) can be measured in relative weight components, and range from 1:1 to 1:50, inclusive thereof.

The formulations and compositions disclosed herein can consist or consist essentially of the listed ingredients. If the formulations consist essentially of the listed ingredients, other ingredients may be present so long as they do not affect the stability of the vancomycin in the formulation, for example, as measured by assay.

Other suitable formulations for use in the present invention can be found in Remington's Pharmaceutical Sciences, Mace Publishing Company, Philadelphia, Pa., 17th ed. (1985).

Dosages

The concentration of glycopeptide antibiotic (such as vancomycin) or a pharmaceutically acceptable salt in the formulation is about 1 mg/mL to about 10 mg/mL and N-acetyl-methionine (such as N-acetyl-D-methionine, N-acetyl-L-methionine, or a combination) thereof in a concentration of about 1 mg/mL to about 5 mg/mL by weight.

The active compound is effective over a wide dosage range and is generally administered in a pharmaceutically effective amount. It will be understood, however, that the amount of the compound actually administered will be determined by a physician, in the light of the relevant circumstances, including the condition to be treated, the chosen route of administration, the actual compound administered and its relative activity, the age, weight, and response of the individual patient, the severity of the patient's symptoms, and the like.

Suitable doses are in the general range of from 0.01-100 mg/kg/day, preferably 0.1-50 mg/kg/day. For an average 70 kg human, this would amount to 0.7 mg to 7 g per day, or preferably 7 mg to 3.5 g per day. In some embodiments, the preferred dosage is no less than 15 mg/kg/day.

Suitable doses and dosage regimens can be determined by range-finding techniques which are a function of the subject's mass, body volume, body surface area, regions of administration, routes of administration, and the degree of cancer prognosis of the subject. Generally, treatment is initiated with smaller dosages that are less than the optimum dose of the composition of the present invention. Thereafter, the dosage is increased by small increments until the optimum effect under the circumstances is reached. The present method can involve the administration of about 100 mg to about 3 grams total to the subject, preferably from about 500 mg to about 2 grams total to the subject.

To reduce the risk of infusion-related adverse reactions, the formulations and compositions of this disclosure when administered intravenously (IV) to the subject or patient can be administered for at least 60 minutes or more. In some embodiments, the formulations and compositions can be administered by IV to the subject or patient at a rate of 10 mg/min or less to reduce infusion-related adverse events. Other patient factors, such as age or obesity, may call for modification of the usual intravenous daily dose.

In some embodiments, the injection concentration of the formulations and compositions (such as a formulation or composition comprising vancomycin and N-acetyl methionine) can be about 1 mg/mL or less or about 5 mg/mL or less. In some embodiments, the injection concentration can be about 1 mg/mL to about 5 mg/mL. In some embodiments, the injection concentration can be about 0.5 mg/mL, 1 mg/mL, about 2 mg/mL, 3 mg/mL, 4 mg/mL or 5 mg/mL.

In some embodiments, the daily dose for an adult subject or patient is 2 grams divided either as 500 mg every 6 hours or 1 g every 12 hours. In some embodiments, the initial daily dose is at least about 15 mg/kg. In some embodiments, the daily dose for a child is 10 mg/kg per dose every 6 hours using a 500 mg vancomycin in 100 mL of solution, 750 mg vancomycin in 150 mL of solution, 1 gram vancomycin in 200 mL of solution, 1.25 gram vancomycin in 250 mL of solution, 1.5 gram vancomycin in 300 mL of solution, 1.75 gram vancomycin in 350 mL of solution, or 2 gram vancomycin in 400 mL of solution in a single-dose bag containing the formulations or compositions described herein.

Accordingly, this invention provides methods for treating infectious diseases, including those caused by Gram-positive organisms, in mammals. The compounds and compositions of this disclosure are particularly useful in treating infections caused by methicillin-resistant staphylococci. Also, the compounds and compositions are useful in treating infection due to enterococci, including vancomycin-resistant enterococci (VRE). Examples of such diseases are severe staphylococcal infections, for example, staphylococcal endocarditis and staphylococcal septicemia. In some embodiments, the compounds and compositions of this disclosure are effective at treating coagulase negative staph. In some embodiments, the compounds and compositions of this disclosure are effective at treating MRSA, enterocolitis, rheumatic fever, endocarditis, and/or colitis. The animal may be either susceptible to, or infected with, the microorganism. The method comprises administering to the animal an amount of a compound of this invention, which is effective for this purpose. In general, an effective amount of a compound of this invention is a dose between about 0.5 and about 100 mg/kg. A preferred dose is from about 1 to about 60 mg/kg of active compound. A typical daily dose for an adult human is from about 50 mg to about 5 g.

In practicing this method, the antibiotic can be administered in a single daily dose or in multiple doses per day. The treatment regimen may require administration over extended periods of time, for example, for several days or for from one to six weeks. The amount per administered dose or the total amount administered will depend on such factors as the nature and severity of the infection, the age and general health of the patient, the tolerance of the patient to the antibiotic and the microorganism or microorganisms in the infection.

In some embodiments, compositions comprising vancomycin of this disclosure can be administered systemically, such as by intravenous, intra-arterial or intraperitoneal administration, such that the final circulating concentration is from approximately 0.001 to approximately 150 micromolar, or higher up to 200, 300, 400, 500, 600, 700, 800, 900 or 1000 micromolar. The final circulating concentration can be 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 100, 110, 120, 130, 140, or 150 micromolar, or any concentration between any of the two recited numbers, or higher as described above and any concentration within the ranges noted. As mentioned herein, the invention also comprises combination therapies in which one or more additional active agent is also administered to a subject. Skilled persons will appreciate desirable dosages for the one or more active agent having regard to the nature of that agent and the principles discussed herein before.

In another embodiment, compositions comprising vancomycin may be used in the invention alone or in combination with one or more additional glycopeptides described herein in the use in the treatment of a particular disorder. Co-administration may allow for improved alleviation or amelioration of one or more symptoms, reduction of the length or extent of a disease, delay or slowing of the progression of disease, amelioration, palliation or stabilization of the disease state, partial or complete remission, prolonged survival and/or other beneficial therapeutic results. Such treatments may be administered simultaneously or sequentially in any order with a period of time between administrations. One of skill in the art will readily appreciate methods of administering agents or therapies simultaneously or sequentially and possible time periods between administrations. The therapies may be administered by the same or different routes.

Manufacture and Stability

In some embodiments, the formulations and compositions of this invention are substantially pure. By substantially pure is meant that the formulations comprise less than about 15%, about 10%, about 5%, or about 1%, and preferably less than about 0.1%, of any impurity. In some embodiments, the total impurities, including metabolites of vancomycin and/or N-acetyl-methionine (such as N-acetyl-D-methionine, N-acetyl-L-methionine, or a combination thereof) will be not more than about 15%. In some embodiments, the total impurities will be not more than about 12%. In some embodiments, the total impurities will be not more than about 11%. In other embodiments, the total impurities will be not more than about 10%.

In some embodiments, the purity of the formulations and compositions of this invention may be measured using a method that includes, for example, an ion exchange HPLC (AEX-HPLC), mass spectrometry, or a combination thereof. Mass spectrometry may include LC/MS or LC/MS/MS. In some embodiments, the method used to measure the impurity may comprise both AEX-HPLC and LC/MS.

Sterile compositions of this invention can be prepared using aseptic processing by dissolving the compound in the formulation vehicle. In one embodiment, the formulation may also be sterilized by filtration. Excipients used in the manufacture of the formulations of this invention are widely used in pharmaceutical products and released to pharmacopeial standards.

EXAMPLES

Example 1: Example Vancomycin Hydrochloride Injection Composition with N-Acetyl-D-Methionine Table 1 below provides a listing of exemplary ingredients/components suitable for an exemplary formulation of the composition of the invention and a desired weight/volume percentage for those ingredients/components.

TABLE 1

| Component No. | Name of Ingredients | Percentage (w/v) |
| --- | --- | --- |
| 1 | Vancomycin Hydrochloride | 0.1 to 1.0 |
| 2 | N-Acetyl-Methionine | 0.1 to 5.0 |
| 3 | Sodium Chloride | 0.005 to 0.1 |
| 4 | Hydrochloric acid | QS* to adjust pH to about 4.5 to about 5.5 |
| 5 | Sodium Hydroxide | QS to adjust pH to about 4.5 to about 5.5 |
| 6 | Water for Injection | QS to 100% |

*QS = Quantum satis = Add as much of the specified ingredient/composition as is needed to achieve the desired result, but not more.

Example 2: Example Vancomycin Hydrochloride Injection Composition with N-Acetyl-D-Methionine Table 2 below provides a list of ingredients/components of another representative formulation of the invention.

TABLE 2

| Component No. | Name of Ingredients | Percentage (w/v) |
| --- | --- | --- |
| 1 | Vancomycin Hydrochloride | 0.51 |
| 2 | N-Acetyl-D-Methionine (NADM) | 2.5 |
| 3 | Sodium Chloride | 0.01 |
| 4 | Hydrochloric acid | QS* to adjust pH to about 4.5 to about 5.5 |
| 5 | Sodium Hydroxide | QS to adjust pH to about 4.5 to about 5.5 |
| 6 | Water for Injection | QS to 100% |

*QS = Quantum satis = Add as much of the specified ingredient/composition as is needed to achieve the desired result, but not more.

The formulation of Example 2 is made by the following steps:

1. In a suitable container, add 5.13 mg of vancomycin hydrochloride to 800 mL of sterile water for injection;
2. Stir until the vancomycin hydrochloride is fully dissolved by visual inspection;
3. Add 25 mg of N-acetyl-D-methionine (NADM) and stir until the NADM is fully dissolved by visual inspection;
4. Add 120 mg of sodium chloride and stir until the sodium chloride is fully dissolved by visual inspection;
5. Stir for additional 5 minutes;
6. Adjust the pH to 5.0, using 1.0 N Hydrochloric acid or sodium hydroxide;
7. QS with water for injection to 1000 mL;
8. Stir for an additional 5 minutes; and
9. Aseptically fill the prepared solution into sterile bags of appropriate size.

In some aspects, the order of solubilizing vancomycin (or a pharmaceutically acceptable salt thereof (such as vancomycin hydrochloride)), sodium chloride (NaCl), and/or N-acetyl-D-methionine can be performed in any order (i.e., first dissolve NaCl, then dissolve vancomycin or N-acetyl-D-methionine, then dissolve the remaining component; or first dissolve vancomycin, then dissolve either N-acetyl-D-methionine or NaCl, then dissolve the remaining component).

In some aspects, the composition will have an osmolality. Osmolality is a measure of solubility of a solution (in wt.). In some aspects, the solubility of the solution can be measured as per the osmolarity, which is the molar solubility of a solution. In some aspects, the osmolality of the compositions of this disclosure can range from about 100 milliosmoles per kilogram (mOsm/kg) of solution to about 1000 mOsm/kg of solution. In some aspects, the osmolality of the composition can range from about 275 mOsm/kg of solution to about 295 mOsm/kg of solution.

In some aspects, the composition will have a conductivity. The conductivity of the aqueous composition can range from about 0.5 S/cm (all conductivities are presented at 25° C.) to about 50 mS/cm. In some aspects, the conductivity of the solution can range from about 200 S/cm to about 5 mS/com, inclusive thereof.

Example 3: Example Vancomycin Hydrochloride Injection Composition with N-Acetyl-D-Methionine Table 3 below provides a list of ingredients/components of another representative formulation of the invention.

TABLE 3

| Component No. | Name of Ingredient | Percentage (w/v) |
| --- | --- | --- |
| 1 | Vancomycin Hydrochloride | 0.51 |
| 2 | N-Acetyl-D-Methionine | 1.5 |
| 3 | Sodium Chloride | 0.01 |
| 4 | Hydrochloric acid | QS* to adjust to about pH 4.5 |
| 5 | Sodium Hydroxide | QS to adjust to about pH 4.5 |
| 6 | Water for Injection | QS to 100% |

*QS = Quantum satis = Add as much of the specified ingredient/composition as is needed to achieve the desired result, but not more.

The formulation of Example 3 is made by the following steps:
1. In a suitable container, add 5.13 mg of vancomycin hydrochloride to 800 mL of water for injection;
2. Stir till vancomycin hydrochloride is fully dissolved by visual inspection;
3. Add 15 mg of N-acetyl-D-methionine (NADM) and stir until the NADM is fully dissolved by visual inspection;
4. Add 120 mg of sodium chloride and stir until the sodium chloride is fully dissolved by visual inspection;
5. Stir for additional 5 minutes;
6. Adjust the pH to 4.5, using 1.0N Hydrochloric acid or sodium hydroxide;
7. QS with water for injection to 1000 mL;
8. Stir for additional 5 minutes; and
9. Aseptically fill the prepared solution into sterile bags of appropriate size.

Example 4: Example Vancomycin Hydrochloride Injection Composition with N-Acetyl-D-Methionine Additional embodiments of vancomycin HCl injection compositions with NADM and saline were prepared by the methods described above, with the following compositions in Tables 4 & 5, respectively:

TABLE 4

| Component No. | Name of Ingredient | Percentage (w/v) |
| --- | --- | --- |
| 1 | Vancomycin Hydrochloride | 0.51 |
| 2 | N-Acetyl-D-Methionine (NADM) | 2.0 |
| 3 | Sodium Chloride | 0.2 |
| 4 | Hydrochloric acid | QS to adjust to about pH 4.5 to 5.5 |
| 5 | Sodium Hydroxide | QS to adjust to about pH 4.5 to 5.5 |
| 6 | Water for Injection | QS to 100% |

TABLE 5

| Component No. | Name of Ingredients | Percentage (w/v) |
| --- | --- | --- |
| 1 | Vancomycin Hydrochloride | 0.51 |
| 2 | N-Acetyl-D-Methionine (NADM) | 2.5 |
| 3 | Sodium Chloride | 0.1 |
| 4 | Hydrochloric acid | QS* to adjust to about pH 4.5 to about pH 5.5 |
| 5 | Sodium Hydroxide | QS to adjust to about pH 4.5 to about pH 5.5 |
| 6 | Water for Injection | QS to 100% |

Example 5: Stability Testing of Representative Formulations as Measured in Glass Vials The formulations prepared according to the invention as described in the above examples were charged for stability under typical and/or accelerated conditions to determine the effect of different factors such as pH of the formulation, ratio of vancomycin to N-acetyl-D-methionine on the formulations. Also, simple vancomycin solutions were prepared in water (where NO NADM was added) and adjusted to the indicated pH ranges and charged for stability. The stability condition includes 25° C./60% relative humidity. The solutions were stored in glass vials. The analytical results of the formulations at 25° C. are summarized in Table 6 below.

TABLE 6

Ambient Condition (25° C./60% Relative Humidity (RH)) Stability Data in Glass Vials

| Time | Vancomycin pH 3.0 | Vancomycin pH 4.0 | Vancomycin pH 4.5 | Vancomycin pH 5.0 | Vancomycin + NADM (15 mg/mL) @ pH 4.5 | Vancomycin + NADM (25 mg/mL) @ pH 4.5 |
| --- | --- | --- | --- | --- | --- | --- |
| Initial/0 | 103.3 | 103.1 | 104.8 | 103.6 | 95.2 | 102 |
| 2 weeks | 85.8 | 91.7 | 93.3 | 92.4 | — | — |

As shown in Table 6 above, the results from the 3 months room temperature study experiment showed that the vancomycin solutions having pH of about 4.5 and 5.0, prepared according to the methods described herein, are stable formulations. The results demonstrate that representative formulations of the invention are at least stable as reference formulations.

Example 6: Stability Testing of Representative Formulations as Measured in Glass Vials and Plastic Bags at Elevated Temperature Formulations prepared as described herein were further studied at pH of about 4.5 to 5.0 in glass vial and plastic bag (PVC (polyvinyl chloride) or PP (polypropylene)) at room temperature (25° C.). The compositions were introduced into vials or bags and then placed in stability chambers. At the appropriate time points, they were withdrawn and analyzed for API assay by HPLC. The bags were PP BAGS FOR READY-TO-USE SOLUTION from Technoflex, FR. A 6-month stability study was conducted and the observed results are set forth in Table 7.

TABLE 7

Vancomycin (5 mg/mL) Stability Data in Vials and Bags at 25° C./60% RH.

|  |  | Vancomycin HCl + 25 mg/mL NAM at pH 5.0 in PP bags | | Vancomycin HCl + 25 mg/mL NAM at pH 5.0 in PVC bags | | Vancomycin HCl + 25 mg/mL NAM at pH 5.0 in vials | | Vancomycin HCl + 25 mg/mL NAM at pH 4.5 in vials | | Vancomycin HCl at pH 4.5 in vials (Control Formulation Without Stabilizer) | |
| --- | --- | --- | --- | --- | --- | --- | --- | --- | --- | --- | --- |
|  |  | pH | Assay | pH | Assay | pH | Assay | pH | Assay | pH | Assay |
| 25° C. | Initial/0 | 5.03 | 106.9 | 5.05 | 106.7 | 5.12 | 106.9 | 4.62 | 108 | 4.44 | 106.3 |
|  | 1 M | 4.98 | 106.2 | 4.98 | 106.6 | 4.98 | 105.4 | 4.51 | 102.1 | 4.94 | 81.9 |
|  | 3 M | 4.99 | 107.1 | 5.03 | 110.3 | 5.0 | 105.1 | 4.53 | 100.7 | Precipitate observed. Stability Discontinued | |
|  | 6 M | 4.99 | 106.2 | 5.03 | 110 | 5.0 | 104.2 | 4.54 | 98.6 | | |

The results indicate that vancomycin-NAM compositions with a pH of 5.0 are significantly more stable that the compositions at pH 4.5. In addition, all other conditions the same, the compositions were as stable in bags as they were in glass vials, indicating that any stability from glass vials is equivalent to the same stability in bags.

There was a slight increase in the concentration of vancomycin in PVC bags relative to PP bags due to water loss, as bags are semi-permeable containers. Additionally, permeabilities of different materials will be different.

Example 7: Pharmacokinetics Study

A subchronic IV/systemic study in a rat model is performed where the animals are dosed via the tail vein daily for 28 days to determine the potential for systemic toxicity. The rat was chosen as it has been successfully used in other NADM non-clinical studies. A 28-day study duration provides a conservative toxicological exposure period as per ICH M3 (FDA/ICH. 2010. M3(R2) Nonclinical Safety Studies for the Conduct of Human Clinical Trials and Marketing Authorization for Pharmaceuticals (FDA 2010)).

The study cohorts (M—male, F—female) are shown below in Table 8. Parameters to evaluate include morbidity/mortality, clinical observations, body weight, food consumption, ophthalmology, hematology, clinical chemistry, urinalysis (including water intake and analysis for NADM and metabolites), organ weight, gross pathology, and histopathology. In addition, toxicokinetic (TK) analyses are performed on samples collected on study days 1 and 28. The TK samples will provide information on systemic exposure and parameters, such as the maximum serum concentration that a drug achieves in a tested area or a specified compartment after the drug has been administered and before the administration of a second dose (Cmax) and the amount of time that a drug is present at the maximum concentration in serum (Tmax). The maximum daily dose (MDD) for humans for NADM is about 0.17 g/kg/day (10 g/day for 60 kg person=0.167 g/kg/day), which translates to a rat equivalent dose of about 1.05 g/kg/day (FDA. 2005a. Guidance for Industry Estimating the Maximum Safe Starting Dose in Initial Clinical Trials for Therapeutics in Adult Healthy Volunteers. Center for Drug Evaluation and Research (CDER). July 2005 (FDA 2005a); calculated by dividing the human MDD by the rat-to-human conversion factor of 0.16). The high dose in this rat study therefore should be at least about 3.15 grams NADM/kg/day to allow for an about 3× margin of safety over the human equivalent maximum clinical dose. Without undue burden, the experiment can be performed on a range of dosages as described herein.

TABLE 8

| Group | Dose (mg/kg/day) | Main Study - # animals | TK Study - # animals |
| --- | --- | --- | --- |
| Control (product solution without impurities or API) | 0 | 10 M / 10 F (20) | 3 M / 3 F (6) |
| Low NADM | TBD | 10 M / 10 F (20) | none |
| Mid NADM | TBD | 10 M / 10 F (20) | 3 M / 3 F (6) |
| High NADM | TBD | 10 M / 10 F (20) | 3 M / 3 F (6) |

Example 8. Demonstration of Antibacterial Activity of Representative Compositions of the Invention In Vitro First, the minimal inhibitory concentration (MICs) of the vancomycin in the compositions of this disclosure are determined.

Bacterial strains from either American Type Tissue Culture Collection (ATCC) or the Centers for Disease Control (CDC), or the Mayo Clinic are obtained and used as described herein.

Minimal inhibitory concentrations (MICs) are measured in a microdilution broth procedure under NCCLS (National Committee for Clinical Laboratory Standards) guidelines (Ginocchio, C., "Role of NCCLS in antimicrobial susceptibility testing and monitoring," Am. J. Health Syst. Pharm., 2002 Apr. 15; 59(8 Suppl 3):57-11. doi: 10.1093/ajhp/59.suppl_3.S7. The compositions are serially diluted into Mueller-Hinton broth in 96-well microtiter plates. Overnight cultures of bacterial strains are diluted based on absorbance at 600 nm so that the final concentration in each well was $5 \times 10^6$ cfu/mL. At a selected timepoint, MICs are determined by visual inspection of the plates Strains routinely tested in the initial screen included methicillin-sensitive *Staphylococcus aureus* (MSSA), methicillin-resistant *Staphylococcus aureus*, methicillin-sensitive *Staphylococcus epidermidis* (MSSE), methicillin-resistant *Staphylococcus epidermidis* (MRSE), vancomycin sensitive *Enterococcus faecium* (VSE Fm), vancomycin sensitive *Enterococcus faecalis* (VSE Fs), vancomycin resistant *Enterococcus faecium* also resistant to teicoplanin (VRE Fm Van A), vancomycin resistant *Enterococcus faecium* sensitive to teicoplanin (VRE Fm Van B), vancomycin resistant *Enterococcus faecalis* also resistant to teicoplanin (VREFs Van A), vancomycin resistant *Enterococcus faecalis* sensitive to teicoplanin (VRE Fs Van B), *Enterococcus gallinarium* of the Van A genotype (VRE Gm Van A), *Enterococcus gallinarium* of the Van C-1 genotype (VRE Gm Van C-1), *Enterococcus casseliflavus* of the Van C-2 genotype (VRE Cs Van C-2), *Enterococcus flavescens* of the Van C-2 genotype (VRE Fv Van C-2), and penicillin-sensitive *Strep-* tococcus pneumoniae (PSSP) and penicillin-resistant *Streptococcus pneumoniae* (PSRP). Compositions which have significant activity against the strains set forth above are then tested for MIC values in a larger panel of clinical isolates including the species listed above and non-speciated coagulase negative *Staphylococcus* both sensitive and resistant to methicillin (MS-CNS and MR-CNS). Those compositions are also were tested for MICs against gram negative organisms, such as *Escherichia coli* and *Pseudomonas aeruginosa*.

The vancomycin-comprising compositions of this invention are expected to be active in the above in vitro test and demonstrate a broad spectrum of activity.

In Vivo Determination of Antibacterial Activity

Tolerability Studies in Mice

A vancomycin-comprising composition as described herein is administered either intravenously or subcutaneously to a first cohort of mice and observed for 5-15 minutes. The dose is increased to a second cohort of mice upon the observation of no adverse effects in the first cohort. The dose incrementation is to be continued until mortality occurred, or the dose is maximized. Dosing begins at 15 mg/kg and increases until the maximum tolerated dose (MTD) is achieved.

Mouse Septicemia Model

An appropriately virulent strain of bacteria (most commonly *S. aureus*, or *E. Faecalis* or *E. Faecium*) is administered to mice (N=10 mice per group) intraperitoneally. The bacteria is combined with hog gastric mucin to enhance virulence. The dose of bacteria (normally $10^6$-$10^7$ bacterial particles) is sufficient to induce mortality in all of the mice over a three day period. One hour after the bacteria is administered, a vancomycin-comprising composition as described herein is administered in a single dose either IV or subcutaneously. Each dose is administered to groups of 10 mice, at doses that range from a maximum of about 15 mg/kg to a minimum of less than 1 mg/kg. A positive control (normally vancomycin with vancomycin sensitive strains) is administered in each experiment. The (EC50) dose at which approximately 50% of the animals are saved is calculated from the results.

Neutropenic Thigh Model

An appropriately virulent strain of bacteria (most commonly *S. aureus*, or *E. Faecalis* or *E. Faecium*, sensitive or resistant to vancomycin) is administered to a first cohort of mice. Mice are initially rendered neutropenic by administration of cyclophosphamide at 200 mg/kg on day 0 and day 2. On day 4 they are infected in the left anterior thigh by an IM injection of a single dose of bacteria. The mice are then administered a vancomycin-comprising composition of this disclosure at a selected time (e.g., one hour) after the bacteria and at various other selected time s (e.g., 1, 2, 4 and 24 hours) the mice are sacrificed (minimum of 3 per time point) the thigh excised, homogenized and the number of CFUs (colony forming units) are determined by plating. Blood is also plated to determine the CFUs in the blood.

The vancomycin-comprising compositions of this invention are expected to be active in the above in vivo test and demonstrate abroad spectrum of activity.

It will be understood that the foregoing description is of exemplary embodiments of this invention, and that the invention is not limited to the specific forms shown. Modifications may be made in the design and arrangement of the elements without departing from the scope of the invention.

The invention described and claimed herein have many attributes and embodiments including, but not limited to, those set forth or described or referenced in this Detailed Description. It is not intended to be all-inclusive and the inventions described and claimed herein are not limited to or by the features or embodiments identified in this Detailed Description, which is included for purposes of illustration only and not restriction. A person having ordinary skill in the art will readily recognize that many of the components and parameters may be varied or modified to a certain extent or substituted for known equivalents without departing from the scope of the invention. It should be appreciated that such modifications and equivalents are herein incorporated as if individually set forth. The invention also includes all of the steps, features, compositions and compounds referred to or indicated in this specification, individually or collectively, and any and all combinations of any two or more of said steps or features.

All patents, publications, scientific articles, web sites, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety. Applicants reserve the right to physically incorporate into this specification any and all materials and information from any such patents, publications, scientific articles, web sites, electronically available information, and other referenced materials or documents. Reference to any applications, patents and publications in this specification is not, and should not be taken as, an acknowledgment or any form of suggestion that they constitute valid prior art or form part of the common general knowledge in any country in the world.

The specific methods and compositions described herein are representative of preferred embodiments and are exemplary and not intended as limitations on the scope of the invention. Other objects, embodiments, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of this, any of the terms "comprising", "consisting essentially of", and "consisting of" may be replaced with either of the other two terms in the specification. Also, the terms "comprising", "including", containing", etc. are to be read expansively and without limitation. The methods and processes illustratively described herein suitably may be practiced in differing orders of steps, and that they are not necessarily restricted to the orders of steps indicated herein or in the claims. It is also that as used herein and in the appended claims, the singular forms "a," "an," and "the" include plural reference unless the context clearly dictates otherwise. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants. Furthermore, titles, headings, or the like are provided to enhance the reader's comprehension of this document, and should not be read as limiting the scope of this. Any examples of embodiments, embodiments or components of the invention referred to herein are to be considered non-limiting.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although this has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any patient matter from the genus, regardless of whether or not the excised material is specifically recited herein.

Other embodiments are within the following claims. In addition, where features or embodiments of the invention are described in terms of Markush groups, those skilled in the art will recognize that the invention is also thereby described in terms of any individual member or subgroup of members of the Markush group.

What is claimed is:

1. A method of treating one or more bacterial infections in a subject in need thereof, the method comprising administering to the subject a liquid formulation that comprises: (a) a therapeutically effective amount of a vancomycin antibiotic or a pharmaceutically acceptable salt thereof, (b) N-acetyl-methionine and (c) one or more pharmaceutically acceptable excipients, wherein the liquid formulation does not include N-acetyl D-alanine or polyethylene glycol-400 or both N-acetyl D-alanine and polyethylene glycol-400.

2. A method of treating an infectious disease in a subject in need thereof, the method comprising administering to the subject a liquid formulation that comprises: (a) therapeutically effective amount of a vancomycin antibiotic or a pharmaceutically acceptable salt thereof, (b) N-acetyl-methionine, and (c) one or more pharmaceutically acceptable excipients, wherein the liquid formulation does not include N-acetyl D-alanine or polyethylene glycol-400 or both N-acetyl D-alanine and polyethylene glycol-400.

3. A method of treating a subject suffering from an infection caused by Gram-positive organisms, the method comprising administering to the subject in need thereof a liquid formulation that comprises: (a) a therapeutically effective amount of a vancomycin antibiotic or a pharmaceutically acceptable salt thereof, (b) N-acetyl-methionine, and (c) one or more pharmaceutically acceptable excipients, wherein the liquid formulation does not include N-acetyl D-alanine or polyethylene glycol-400 or both N-acetyl D-alanine and polyethylene glycol-400.

4. A method of treating a subject suffering from an inflammatory disease, the method comprising administering to the subject in need thereof a liquid formulation that comprises: (a) a therapeutically effective amount of a vancomycin antibiotic or a pharmaceutically acceptable salt thereof, (b) N-acetyl-methionine, and (c) one or more pharmaceutically acceptable excipients, wherein the liquid formulation does not include N-acetyl D-alanine or polyethylene glycol-400 or both N-acetyl D-alanine and polyethylene glycol-400.

5. The method of claim 1, wherein the vancomycin antibiotic or the pharmaceutically acceptable salt thereof is present in an amount of about 0.1% by weight to about 1.000 by weight, and wherein the weight ratio of vancomycin antibiotic or the pharmaceutically acceptable salt thereof to N-acetyl-methionine in the liquid formulation is about 1:3 by weight to about 1:5 by weight, about 1:1 by weight to about 1:100 by weight, about 1:1 by weight to about 1:50 by weight, or about 1:1 by weight to about 1:10 by weight.

6. The method of claim 1, wherein the vancomycin antibiotic or the pharmaceutically acceptable salt thereof is vancomycin or vancomycin hydrochloride, and the N-acetyl-methionine is N-acetyl-D-methionine, N-acetyl-L-methionine, or a combination thereof.

7. The method of claim 5, wherein the vancomycin antibiotic or a pharmaceutically acceptable salt thereof is vancomycin or vancomycin hydrochloride, and the N-acetyl-methionine is N-acetyl-D-methionine.

8. The method of claim 1, wherein the subject is mammal or human.

9. The method of claim 1, wherein the one or more bacterial infections is one or more skin infections, one or more skin structure infections, one or more bone infections, one or more lower respiratory tract infections, or a combination thereof.

10. The method of claim 1, wherein the administration is parenteral administration.

11. The method of claim 10, wherein the parenteral administration is intramuscular injection, subcutaneous injection, intravenous injection, or intradermal injection.

12. The method of claim 2, wherein the infectious disease is caused by Methicillin-resistant *Staphylococcus aureus* (MRSA), enterococci, vancomycin-resistant enterococci (VRE), coagulase negative staphylococci, or a combination thereof.

13. The method of claim 3, wherein the Gram-positive organisms is *Staphylococcus, Streptococcus* spp., *Enterococcus* spp. or a combination thereof.

14. The method of claim 3, wherein the infection caused by Gram-positive organisms is a staphylococcal infection.

15. The method of claim 14, wherein the staphylococcal infection is staphylococcal endocarditis, staphylococcal septicemia, or a combination thereof.

16. The method of claim 4, wherein the inflammatory disease is enterocolitis, rheumatic fever, endocarditis, colitis, or a combination thereof.

17. A process for preparing a liquid composition for parenteral administration, the process comprising: (a) adding a vancomycin antibiotic or pharmaceutically acceptable salt to sterilized water; (b) stirring the solution until the vancomycin antibiotic or pharmaceutically acceptable salt is fully dissolved by visual inspection; (c) adding N-acetyl-D-methionine (NADM) to the solution and stirring until the NADM is fully dissolved by visual inspection; (d) adding sodium chloride and stirring until the components of the solution are fully dissolved by visual inspection; (e) adjusting the pH to about 5.0 using hydrochloric acid, sodium hydroxide, or both; (f) QS with sterilized water suitable for injection to a selected total volume; and (g) stirring for an additional selected amount of time to form a prepared composition.

18. The process of claim 17, wherein the sterilized water is prepared by one or more of heat sterilization, gaseous sterilization, filtration sterilization, or radiation sterilization.

19. The process of claim 17, further comprising the step of: (h) aseptically filling the prepared solution into sterile bags.

20. The process of claim 17, wherein the relative amount of the vancomycin antibiotic or a pharmaceutically acceptable salt thereof in the prepared liquid composition is about 0.1% by weight to about 1.0% by weight.

21. The process of claim 17, wherein the relative amount of the N-acetyl-methionine in the prepared liquid composition is about 1.5% to about 2.5% by weight.

22. The process of claim 17, wherein the relative amount of the sodium chloride in the prepared solution is about 0.012% by weight.

23. The process of claim 17, wherein the vancomycin antibiotic or the pharmaceutically acceptable salt thereof is vancomycin or vancomycin hydrochloride, and the N-acetyl-methionine is N-acetyl-D-methionine, N-acetyl-L-methionine, or a combination thereof.

24. The process of claim 17, wherein the N-acetyl-methionine is N-acetyl-D-methionine, N-acetyl-L-methionine, or a combination thereof.

\* \* \* \* \*